United States Patent [19]

Ritson

[11] Patent Number: 4,834,744
[45] Date of Patent: May 30, 1989

[54] SPIKE FOR PARENTERAL SOLUTION CONTAINER

[75] Inventor: Carl Ritson, San Jose, Calif.

[73] Assignee: Critikon, Inc., Tampa, Fla.

[21] Appl. No.: 117,009

[22] Filed: Nov. 4, 1987

[51] Int. Cl.⁴ .............................................. A61B 19/00
[52] U.S. Cl. .................................................. 604/411
[58] Field of Search ...................... 604/411, 82, 83, 84, 604/85, 412, 413, 414, 415, 416, 410, 240, 274, 244, 251, 252, 253, 63, 245

[56] References Cited

U.S. PATENT DOCUMENTS

| Re. 32,294 | 11/1986 | Knute | 604/253 |
| 3,868,965 | 3/1975 | Noiles et al. | 604/411 |
| 3,990,443 | 11/1976 | Fletcher | 604/253 |
| 4,038,981 | 8/1977 | LeFevre et al. | 604/253 |
| 4,038,982 | 8/1977 | Burke et al. | 604/253 |
| 4,105,028 | 8/1978 | Sadlier et al. | 604/253 |
| 4,211,588 | 7/1980 | Raines | 604/411 |
| 4,262,671 | 4/1981 | Kersten | 604/411 |
| 4,392,850 | 7/1983 | Elias et al. | 604/414 |
| 4,397,648 | 8/1983 | Knute | 604/253 |
| 4,411,661 | 10/1983 | Kersten | 604/411 |
| 4,474,206 | 10/1984 | Cannon | 604/253 |
| 4,675,020 | 6/1987 | McPhee | 604/414 |
| 4,680,977 | 7/1987 | Conero et al. | 604/253 |
| 4,718,896 | 1/1988 | Arndt et al. | 604/253 |

Primary Examiner—John D. Yasko
Attorney, Agent, or Firm—W. Brinton Yorks, Jr.

[57] ABSTRACT

A parenteral solution container spike is provided which accesses a solution container with a pointed end, provides means for attaching a drip chamber at the other end with a drop former extending from the spike into the drip chamber, and an annular projection extending outward from the drip chamber end of the spike for attaching to a droplet detector with the drip chamber properly positioned in the droplet detector.

8 Claims, 3 Drawing Sheets

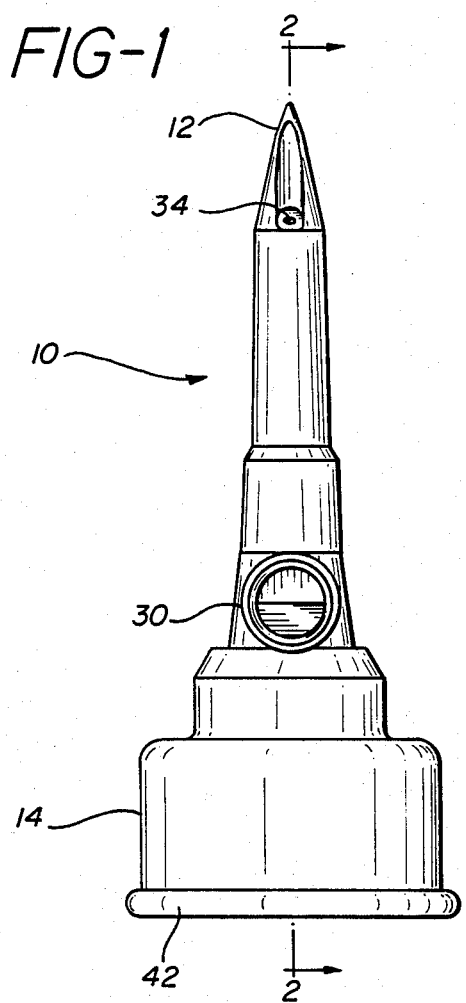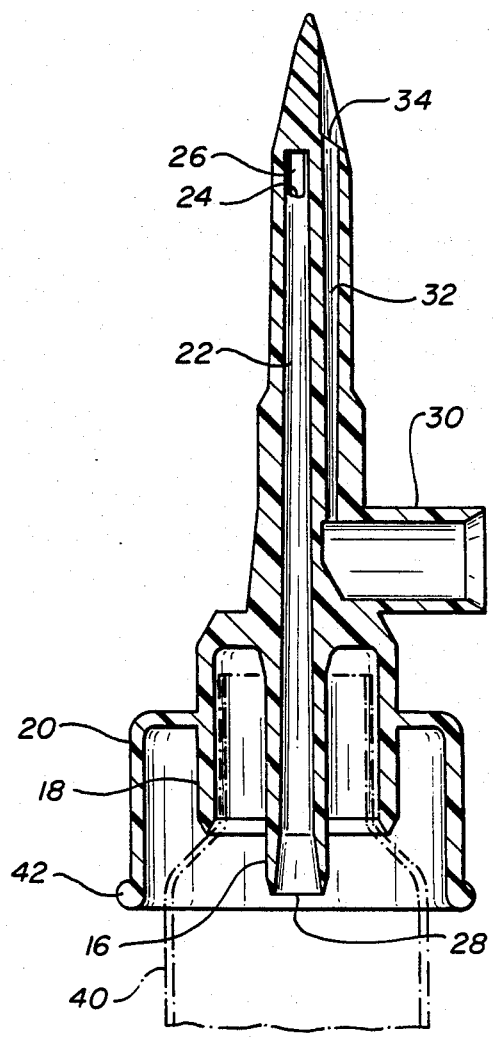

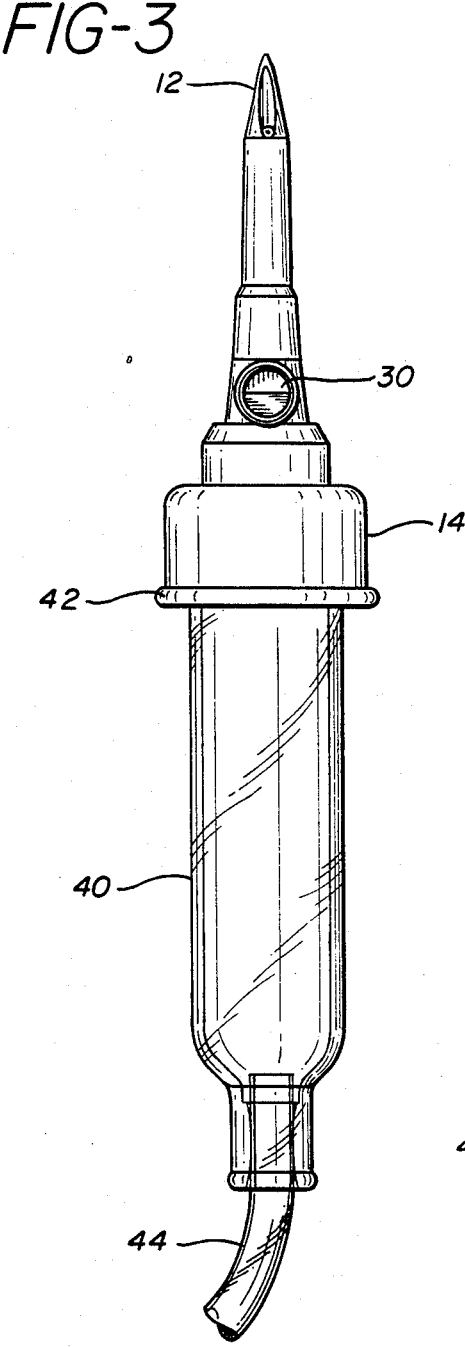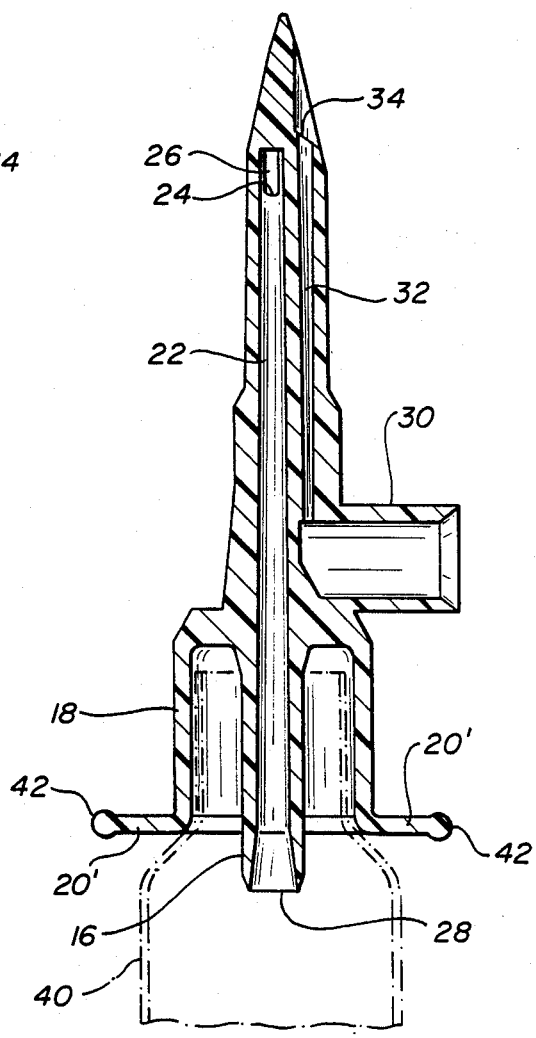

SPIKE FOR PARENTERAL SOLUTION CONTAINER

This invention relates to spikes for accessing containers of solutions to be infused into a medical patient and, in particular, to spikes which are used in conjunction with drip chambers for the counting of parenteral solution droplets.

Many currently available devices for infusing parenteral solutions monitor the volume of fluid being infused by counting fluid droplets falling in a drip chamber. The parenteral solution is contained in a bottle or bag suspended above the infusion site. Access to the bottle or bag is gained by penetrating a membrane on the container with a sterile spike. The spike contains a passageway whereby the solution is conducted through the spike and I.V. tubing to a drip chamber. At the top of the drip chamber is a specially designed port at which droplets form and then fall to the bottom of the chamber, where the solution will then be conducted through tubing to the infusion site. As the droplets fall through the drip chamber they interrupt an optical beam directed through the chamber. Interruptions of the beam are optically detected and converted to electrical signals, which are recorded to measure the amount of fluid passing through the drip chamber to the infusion site.

In accordance with the principles of the present invention, a parenteral solution container spike is provided which cooperates with and retains a drip chamber and a droplet counter. The spike also provides an integral portion of the drip chamber The spike comprises a pointed segment at its distal end which is used to access the parenteral solution bottle or bag. At its proximal end the spike connects with a drip chamber, forming the top of the chamber and providing the port at which fluid droplets are formed. Also provided at the proximal end is means for connecting the spike to a droplet counter. The spike thus supports both the drip chamber and the droplet counter, and does so in a manner that fixes the drop former port and drop detection optics in a predetermined relationship which provides accurate droplet detection.

In the drawings:

FIG. 1 illustrates a parenteral solution container spike of the present invention;

FIG. 2 illustrates the spike of FIG. 1 in cross-section;

FIG. 3 illustrates a spike of the present invention connected to a drip chamber:

FIG. 6 illustrates an alternate embodiment of the present invention.

Figure 4:
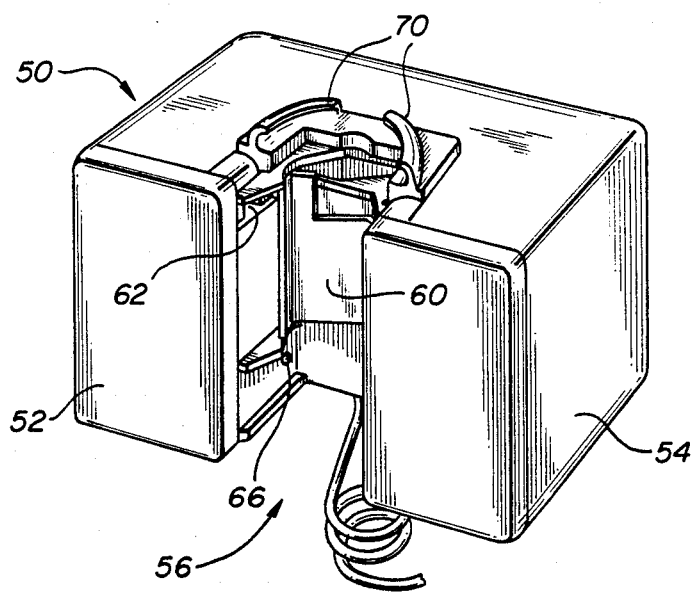
FIG. 4 illustrates a droplet detector adopted for a connection with a spike of the present invention.

Referring to FIGS. 1 and 2, a parenteral solution container spike 10 of the present invention is shown. The cross-sectional view of the spike in FIG. 2 is rotated ninety degrees with respect to the view of FIG. 1. The spike has a pointed distal end 12 which is capable of piercing the access membrane of a parenteral solution bag or bottle. At its proximal end 14 the spike widens to form several hollow concentric sections 16, 18, and 20. Extending through the spike 10 is a fluid passageway 22 which terminates at the distal end at opening 24. An aperture 26 extends through the distal end and transverse to the opening 24. When the distal end of the spike is inserted into the fluid container, the fluid passes freely into the aperture 26 from both sides of the spike and then through opening 24 to the passageway 22. The fluid is thereby conducted to the drop former 16 at the proximal end of passageway 22.

An air vent port 30 is formed on the side of the spike. The port 30 is connected by a passageway 32 to the distal end of the spike, terminating at an opening 34. When the spike is used with a collapsible fluid bag or a vented bottle the vent port 30 is not needed and is plugged. But when the spike is used with a non-vented bottle, it is necessary to vent the bottle to atmospheric pressure so that fluid can flow from the bottle. In that instance an air permeable filter assembly with a microbial barrier is inserted into the vent port 30. The filter is hydrophobic so that it will not become wetted with fluid, and is further protected from wetting by a one-way duckbill valve located inboard of the filter material within the vent port. Air will thus pass through the filter material and the duckbill valve to the passageway 32 to equalize the pressure above the fluid in the bottle to atmospheric pressure.

drop

Fluid passing through passageway 22 flows to the former 16 at the proximal end of the passageway. The end 28 of the tubular drop former 16 is tapered to a sharply defined edge. If the end of the drop former were flat, fluid droplets would spread by adhesion across the flat surface. This would cause an enlargement of drop size, and a resulting incorrect measurement of fluid flow through the drip chamber. The sharp edge of the drop former insures uniform drop size and prevents the migration of fluid around the end of the drop former.

Surrounding the drop former 16 is a cylindrical section 18. The section 18 is used to mount a drip chamber 40, shown in phantom, to the spike 10 and around the drop former. The drip chamber 40 slides securely inside the section 18 and is bonded in place.

Surrounding the cylindrical section 18 and the top of the drip chamber is an outer cylindrical section 20. This section 20 has a flange 42 formed at its proximal end. As explained by the subsequent drawing figures, the section 20 and its flange 42 provide a means for mounting a droplet counter to the spike in a predetermined orientation to the drip chamber.

A full illustration of the spike 10 connected to a drip chamber 40 is shown in FIG. 3. A tubing section 44 extends from the bottom of the drip chamber 40 to conduct fluid to the infusion site.

Referring to FIG. 4, a droplet detector 50 suitable for use with the spike and drip chamber assembly of FIG. 3 is shown. The illustrated droplet detector is commercially available as a component of a Dropminder TM IV infusion system, available from Critikon, Inc. of Tampa, Fla. The droplet detector 50 includes joined left and right compartments 52 and 54 which are separated in the front by a cavity 56. The cavity 56 accommodates a drip chamber and contains a spring hinged door 60. In FIG. 4 a corner of the door 60 is broken away to reveal an aperture 62 behind the upper corner of the door. Located in this aperture 62 is a phototransistor. Directly across the cavity 56 from aperture 62 inside the right compartment 54 is an arcuate array of photodiodes directed at the aperture 62 and its phototransistor. When the cavity 56 is empty the door 60 springs slightly forward, blocking the line of sight between ones of the photodiodes and the phototransistor. Since the phototransistor will be unable to receive light from the photodiodes blocked by the door, the droplet detector will interpret this condition as the absence of a drip chamber. Appropriate indications of this condition will then be displayed by the infusion system.

When a drip chamber is properly mounted in the cavity 56, the drip chamber will push the door to the rear of the cavity exposing the phototransistor to light from all of the photodiodes in the array. The droplet detector will then be able to detect the proper installation of the drip chamber by the reception of light from all of the photodiodes in the array.

Located below the door 60 in cavity 56 is an aperture 66 containing another phototransistor. The aperture 66 opposes a similar aperture on the other side of the cavity, which contains a photodiode. The light path between aperture 66 and its opposing aperture is intended to be interrupted by the volume of fluid in the lower portion of the drip chamber. This light path thereby provides a means for detecting the fluid level in the drip chamber. During normal operation the fluid in the bottom of the drip chamber is intended to rise to and maintain a level midway between aperture 66 and aperture 62.

Extending from the bottom of the droplet detector 50 is a cable 68. This cable contains wiring which conducts electrical signals between the droplet detector and a central processor which calculates the volume of solution conveyed to the patient.

Located around the top of the cavity 56 is a flexible, two-piece collar 70. The collar provides a mounting means for attaching the droplet detector 50 to a spike and drip chamber. The collar is flexible so that the flange 42 of the spike will snap into the curved inner surface of the collar. The two pieces of the collar extend around approximately 200° of the perimeter of the flange 42. This allows the flange to be easily snapped into the collar and retains the flange securely in place.

Figure 5:
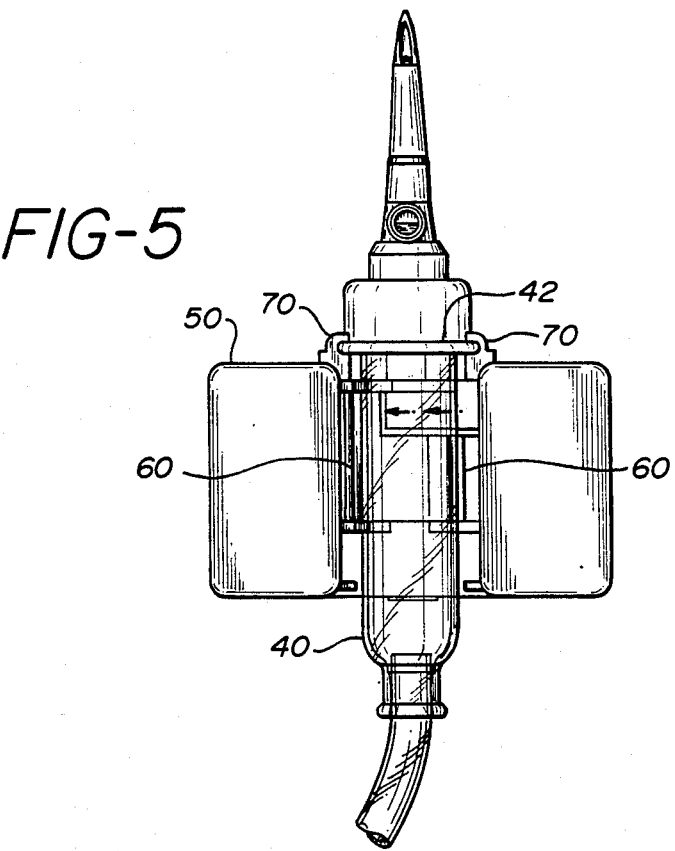
FIG. 5 illustrates the spike and drip chamber of FIG. 3 when connected with the droplet of FIG. 4.

FIG. 5 illustrates the spike and drip chamber of FIG. 3 when mounted with the droplet detector 50 of FIG. 4. The flange 42 of the spike 10 is secured in the collar 70. When attached in this manner, the drip chamber is then properly located in the cavity 56 so that the drip chamber presses the door 60 to the back of the cavity. The properly located drip chamber is aligned in the cavity so that the light beams from the photodiodes which are directed at the phototransistor in aperture 62 pass through the longitudinal center of the drip chamber in a predetermined array. This orients the beams through the central portion of the chamber where the droplets fall from the drop former 16. The paths of the drop detecting light beams are indicated by the arrows in the drip chamber. The properly oriented drip chamber also enables the correct operation of the fluid level detector below the door 60.

In addition to providing the critical geometric relationship between the drip chamber and the droplet detector, the mating flange 42 and collar 70 also provide support for the droplet detector. In normal use, the parenteral solution bottle or bag is hung from a pole. The distal end of the spike is inserted into the fluid container, thereby suspending the spike from the container. The drip chamber 40 is suspended from the annular section 18 of the spike, and the droplet detector 50 is suspended by the collar 70 from the flange 40 of the outer annular section 20. Thus the interconnected spike, drip chamber and droplet detector all hang from the bottle or bag in their proper orientation, without the need for interconnecting tubing or any further supporting items.

FIG. 6 shows an alternate embodiment of the present invention. In this embodiment the outer section 20' at the proximal end of the spike is an annular section projecting outwardly from section 18 and terminating in the annular flange 42. This annular section 20' does not cover the drop former 16 as does the cylindrical section 20 of FIG. 3. This embodiment allows the user to observe the formation of fluid droplets at the end of the drop former 16 during use of the device. As before, use of this embodiment must provide the geometric relationship required of the drip chamber when located in the droplet detector.

What is claimed is:

1. A spike for accessing a container of parenteral solution comprising:
   a pointed distal end having an aperture associated therewith;
   a passageway defined by an interior wall extending through said spike from said aperture to a proximal end of said spike, the proximal end of said passageway terminating in a tubular drop former;
   means located at the proximal end of said spike, and surrounding said drop former, said surrounding means comprising a cylindrical section having a proximal opening for engaging and surrounding the distal end of a drip chamber, whereby said drop former is located within said drip chamber; and
   means, located at the proximal end of said spike and extending outwardly about the periphery of said surrounding means, and including an outer annulus extending outward of the outer diameter of said drip chamber for attaching said spike to a droplet detector.

2. The spike of claim 1, wherein said droplet detector attaching means comprises a disc-shaped member projecting outwardly from said surrounding means.

3. The spike of claim 1, wherein said outer annulus comprises a flange.

4. The spike of claim 1, wherein said disc-shaped member is terminated in a flange.

5. The spike of claim 1, wherein said drop former, said surrounding means, and said droplet detector attaching means each exhibits a generally cylindrical shape.

6. The spike of claim 1, wherein said distal end further comprises means for suspending said spike from said solution container, said surrounding means further comprises means for suspending a drip chamber from said spike, and said droplet detector attaching means further comprises means for suspending a droplet detector from said spike.

7. The spike of claim 1, wherein said droplet detector attaching means further comprises means for orienting said drip chamber with respect to said droplet detector in a predetermined relationship.

8. The spike of claim 1, further comprising:
   a vent port located between said distal and proximal ends of said spike; and
   a second passageway defined by an interior wall of said spike connecting said vent port to a second aperture located in the vicinity of said distal end of said spike.

* * * * *